US012697036B2

(12) United States Patent
Kim

(10) Patent No.: US 12,697,036 B2
(45) Date of Patent: Aug. 4, 2026

(54) METHOD, DEVICE, AND NON-TRANSITORY COMPUTER-READABLE RECORDING MEDIUM FOR EXTRACTING BIOSIGNAL DATA

(71) Applicant: HUINNO, CO., LTD., Seoul (KR)

(72) Inventor: Joo Min Kim, Seoul (KR)

(73) Assignee: HUINNO, CO., LTD., Seoul (KR)

( * ) Notice: Subject to any disclaimer, the term of this patent is extended or adjusted under 35 U.S.C. 154(b) by 505 days.

(21) Appl. No.: 18/464,393

(22) Filed: Sep. 11, 2023

(65) Prior Publication Data

US 2023/0414113 A1 Dec. 28, 2023

Related U.S. Application Data

(63) Continuation of application No. PCT/KR2022/002182, filed on Feb. 15, 2022.

(30) Foreign Application Priority Data

Mar. 12, 2021 (KR) ........................ 10-2021-0033015

(51) Int. Cl.
*A61B 5/0205* (2006.01)
*A61B 5/00* (2006.01)
(52) U.S. Cl.
CPC ............ *A61B 5/0205* (2013.01); *A61B 5/681* (2013.01)
(58) Field of Classification Search
CPC ..... A61B 5/0205; A61B 5/681; A61B 5/0022; A61B 5/02438; A61B 5/318; A61B 5/369; A61B 5/389; A61B 5/7232; A61B 2560/0214; A61B 5/0024; A61B 5/6801; A61B 2560/0209
See application file for complete search history.

(56) References Cited

U.S. PATENT DOCUMENTS

| | | | | | |
|---|---|---|---|---|---|
| 5,627,308 | A | * | 5/1997 | Dahneke | ................. G01P 5/001 73/28.01 |
| 11,172,882 | B2 | * | 11/2021 | Upadhya | .............. A61B 5/6832 |
| 2006/0047990 | A1 | * | 3/2006 | James | ....................... G06F 1/12 713/400 |

(Continued)

FOREIGN PATENT DOCUMENTS

| | | |
|---|---|---|
| KR | 10-2008-0035364 A | 4/2008 |
| KR | 10-2015-0110053 A | 10/2015 |

(Continued)

*Primary Examiner* — Amine Benlagsir
(74) *Attorney, Agent, or Firm* — United One Law Group LLC; Kongsik Kim; Jhongwoo Peck

(57) ABSTRACT

A method for extracting biosignal data is provided. The method includes the steps of: determining whether a data extraction device is connected to a data collection device; and in response to determining that the data extraction device is not connected to the data collection device, determining to establish a data storage path which allows biosignal data collected by the data collection device to be stored in a memory of the data collection device via a microcontroller (MCU) of the data collection device, and in response to determining that the data extraction device is connected to the data collection device, determining to establish a data extraction path which allows an interface of the data extraction device to directly connect to the memory of the data collection device not via the MCU of the data collection device.

7 Claims, 5 Drawing Sheets

(56)     References Cited

U.S. PATENT DOCUMENTS

| | | | | |
|---|---|---|---|---|
| 2006/0187837 A1* | 8/2006 | Warren | ................ | H04L 49/357 |
| | | | | 370/235 |
| 2006/0269294 A1* | 11/2006 | Kikuchi | ............ | H04B 10/5561 |
| | | | | 398/161 |
| 2011/0178759 A1* | 7/2011 | Uchida | ............... | G01C 22/006 |
| | | | | 73/488 |
| 2012/0272839 A1* | 11/2012 | Kaneko | ................ | B30B 15/146 |
| | | | | 100/43 |
| 2014/0240167 A1* | 8/2014 | Cho | ....................... | G08G 1/052 |
| | | | | 342/104 |
| 2015/0277767 A1* | 10/2015 | Hamano | .............. | G06F 3/0665 |
| | | | | 711/114 |
| 2016/0337295 A1* | 11/2016 | Bennett | ................. | G06Q 10/10 |
| 2018/0357166 A1* | 12/2018 | Yu | ........................... | G06F 12/02 |
| 2020/0069252 A1* | 3/2020 | Upadhya | .............. | A61B 5/6813 |
| 2022/0141419 A1* | 5/2022 | Maeda | ................... | H04W 4/40 |
| | | | | 348/148 |

FOREIGN PATENT DOCUMENTS

| | | | | | |
|---|---|---|---|---|---|
| KR | 101560285 | B1 * | 10/2015 | ........... | A61B 5/0456 |
| KR | 10-1572807 | B1 | 12/2015 | | |
| KR | 10-2017-0019745 | A | 2/2017 | | |
| KR | 10-2017-0051134 | A | 5/2017 | | |
| KR | 10-2018-0046762 | A | 5/2018 | | |

* cited by examiner

FIG. 4

METHOD, DEVICE, AND NON-TRANSITORY COMPUTER-READABLE RECORDING MEDIUM FOR EXTRACTING BIOSIGNAL DATA

CROSS-REFERENCE TO RELATED APPLICATIONS

This application is a Continuation of International Application No. PCT/KR2022/002182 filed on Feb. 15, 2022, which claims priority from Korean Patent Application No. 10-2021-0033015 filed on Mar. 12, 2021. The aforementioned applications are incorporated herein by reference in their entireties.

TECHNICAL FIELD

The present invention relates to a method, device, and non-transitory computer-readable recording medium for extracting biosignal data.

RELATED ART

In recent years, wearable devices have been introduced that allow users to easily and conveniently measure a biosignal such as an electrocardiogram, heart rate, pulse, and brain wave at home without visiting hospitals, and to store and transmit data on the measured biosignal, so that physical condition of the users may be remotely monitored and heart abnormality such as arrhythmia may be even diagnosed.

Since wearable devices need to be in constant operation in order to constantly detect or measure biosignals, there is a need to design the wearable devices to have low-power performance. To meet this need, it is common for the components included in a wearable device (e.g., a biosignal sensor, analog signal processing module, microcontroller (MCU), antenna, memory, and data interface) to have low-power performance as well.

However, wearable devices have technical limitations that make them unsuitable for high-speed transmission of large-sized biosignal data continuously sensed or measured over a long period of time (e.g., days to tens of days) to an external data extraction device or a server.

FIG. 1 illustratively shows the configuration of a system for extracting biosignal data from a wearable device according to a conventional technique.

Specifically, referring to FIG. 1, a conventional wearable device 10 reads data stored in a memory and transmits biosignal data to an external data extraction device 20 or a server (not shown) via a data interface provided by a microcontroller (MCU). Since the data interface provided by the microcontroller, which is designed for low power, typically has a low transmission speed (e.g., up to 4 Mbit/sec), it takes a lot of time to extract large-sized biosignal data stored in the wearable device 10. For example, assuming that biosignal data with a resolution of 12 bits is measured at a sampling rate of 500 samples/sec and stored in the memory of the wearable device, the size of the biosignal data stored for 7 days would be about 3.6 Gbit, and it would take a long time of about 907.2 seconds to extract this size of biosignal data at a speed of 4 Mbit/sec (i.e., a speed typically supported by the microcontroller of the wearable device).

In this connection, the inventor(s) present a novel and inventive technique for establishing, when it is determined that a data extraction device is connected to a data collection device (i.e., a wearable device), a data extraction path which allows an interface of the data extraction device to directly connect to a memory of the data collection device not via a microcontroller (MCU) of the data collection device, thereby enabling high-speed transmission of large-sized biosignal data stored in the memory to the external data extraction device, while maintaining low-power performance of the data collection device as the wearable device.

SUMMARY

One object of the present invention is to solve all the above-described problems in the prior art.

Another object of the invention is to enable high-speed transmission of large-sized biosignal data stored in a wearable device to an external data extraction device, while maintaining low-power or light-weighting performance of the wearable device, by determining whether a data extraction device is connected to a data collection device, and in response to determining that the data extraction device is not connected to the data collection device, determining to establish a data storage path which allows biosignal data collected by the data collection device to be stored in a memory of the data collection device via a microcontroller (MCU) of the data collection device, and in response to determining that the data extraction device is connected to the data collection device, determining to establish a data extraction path which allows an interface of the data extraction device to directly connect to the memory of the data collection device not via the MCU of the data collection device.

The representative configurations of the invention to achieve the above objects are described below.

According to one aspect of the invention, there is provided a method for extracting biosignal data, the method comprising the steps of: determining whether a data extraction device is connected to a data collection device; and in response to determining that the data extraction device is not connected to the data collection device, determining to establish a data storage path which allows biosignal data collected by the data collection device to be stored in a memory of the data collection device via a microcontroller (MCU) of the data collection device, and in response to determining that the data extraction device is connected to the data collection device, determining to establish a data extraction path which allows an interface of the data extraction device to directly connect to the memory of the data collection device not via the MCU of the data collection device.

According to another aspect of the invention, there is provided a device for extracting biosignal data, the device comprising: a connection status determination unit configured to determine whether a data extraction device is connected to a data collection device; and a data path management unit configured to, in response to determining that the data extraction device is not connected to the data collection device, determine to establish a data storage path which allows biosignal data collected by the data collection device to be stored in a memory of the data collection device via a microcontroller (MCU) of the data collection device, and in response to determining that the data extraction device is connected to the data collection device, determine to establish a data extraction path which allows an interface of the data extraction device to directly connect to the memory of the data collection device not via the MCU of the data collection device.

In addition, there are further provided other methods and devices to implement the invention, as well as non-transitory computer-readable recording media having stored thereon computer programs for executing the methods.

According to the invention, it is possible to enable high-speed transmission of large-sized biosignal data stored in a data collection device to an external data extraction device.

According to the invention, it is possible to maintain a state in which biosignal data is stored in a memory via a microcontroller operating at low power, when a data extraction device is not connected to a wearable device, thereby enabling high-speed data extraction while maintaining low-power performance of a data collection device as the wearable device.

According to the invention, it is possible to drive a memory of a data collection device at high speed using external power supplied from a data extraction device, so that resources of a wearable device are not consumed even when large-sized biosignal data is extracted.

BRIEF DESCRIPTION OF THE DRAWINGS

FIG. 4 illustratively shows how biosignal data stored in a data collection device is extracted to a data extraction device according to one embodiment of the invention.

DETAILED DESCRIPTION

Figure 1:
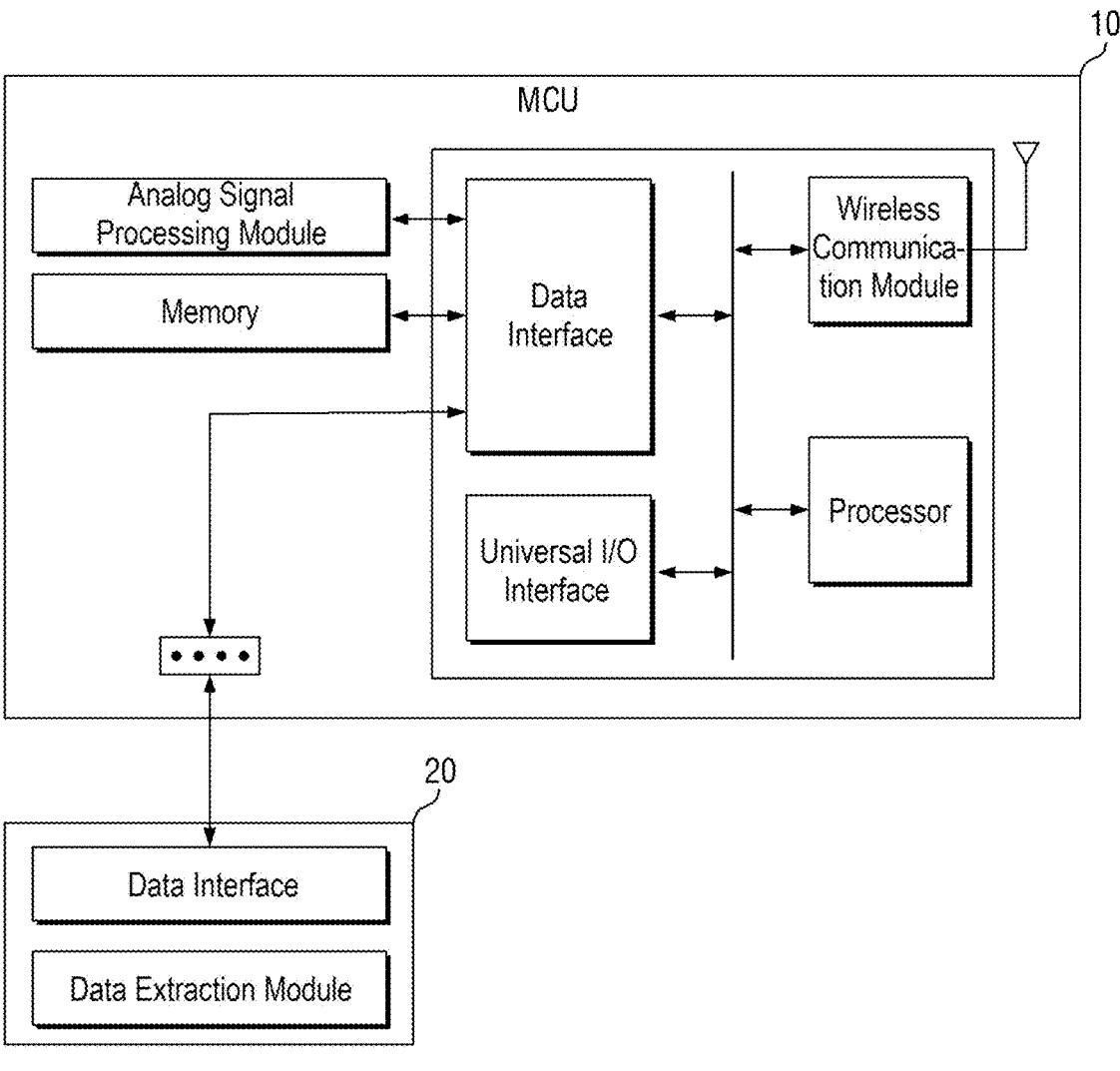
FIG. 1 illustratively shows the configuration of a system for extracting biosignal data from a wearable device according to a conventional technique.

In the following detailed description of the present invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures and characteristics described herein may be implemented as modified from one embodiment to another without departing from the spirit and scope of the invention. Furthermore, it shall be understood that the positions or arrangements of individual elements within each embodiment may also be modified without departing from the spirit and scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, various preferred embodiments of the invention will be described in detail with reference to the accompanying drawings to enable those skilled in the art to easily implement the invention.

Configuration of the Entire System

Figure 2:
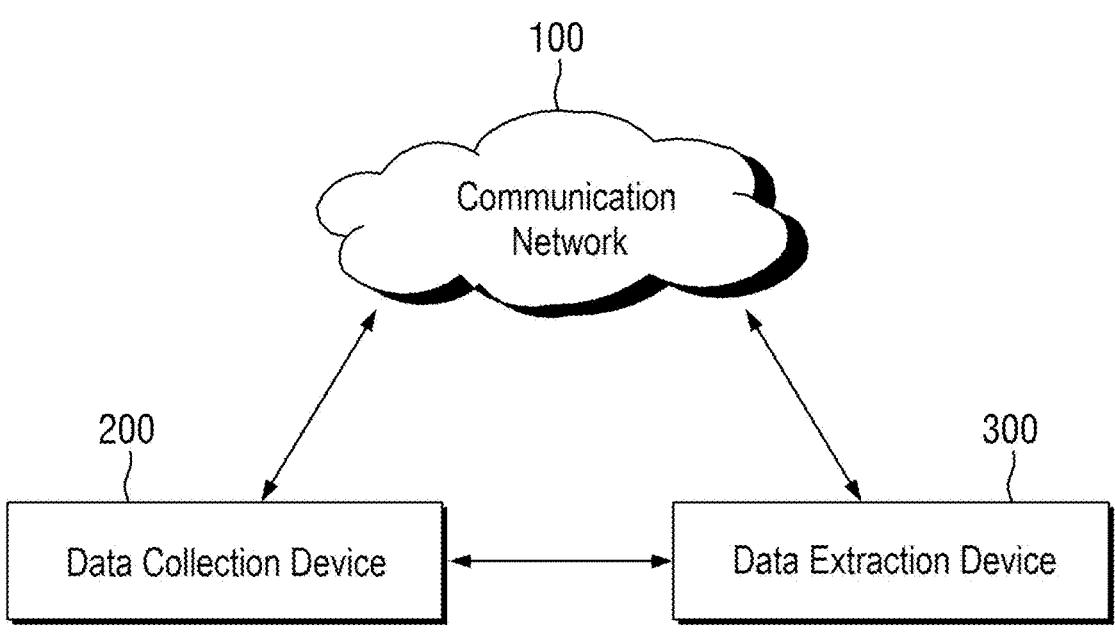
FIG. 2 schematically shows the configuration of an entire system for extracting biosignal data according to one embodiment of the invention FIG. 3 illustratively shows the configuration of a data collection device according to one embodiment of the invention.

FIG. 2 schematically shows the configuration of the entire system for extracting biosignal data according to one embodiment of the invention.

As shown in FIG. 2, the entire system according to one embodiment of the invention may comprise a communication network 100, a data collection device 200, and a data extraction device 300.

First, the communication network 100 according to one embodiment of the invention may be implemented regardless of communication modality such as wired and wireless communications, and may be constructed from a variety of communication networks such as local area networks (LANs), metropolitan area networks (MANs), and wide area networks (WANs). Preferably, the communication network 100 described herein may be the Internet or the World Wide Web (WWW). However, the communication network 100 is not necessarily limited thereto, and may at least partially include known wired/wireless data communication networks, known telephone networks, or known wired/wireless television communication networks.

For example, the communication network 100 may be a wireless data communication network, at least a part of which may be implemented with a conventional communication scheme such as radio frequency (RF) communication, WiFi communication, cellular communication (e.g., Long Term Evolution (LTE) communication), Bluetooth communication (more specifically, Bluetooth Low Energy (BLE) communication), infrared communication, and ultrasonic communication.

Next, the data collection device 200 according to one embodiment of the invention is equipment capable of connecting to and communicating with the data extraction device 300 to be described below, or communicating with another device (not shown) or a server (not shown) via the communication network 100, and any type of equipment having a microcontroller (MCU) for computing capabilities, such as a smart watch and a smart patch, may be adopted as the data collection device 200 according to the invention.

Specifically, the data collection device 200 according to one embodiment of the invention may further include a sensor for sensing or measuring a biosignal from a user's body (e.g., an electrocardiogram sensor, an electromyogram sensor, a heart rate sensor, a brainwave sensor, or a pulse sensor), and a memory for storing data on the biosignal sensed or measured by the sensor. Further, such a measurement sensor may be included in another device interworking with the data collection device 200 via the communication network 100.

Specifically, the data collection device 200 according to one embodiment of the invention may function to determine whether the data extraction device 300 is connected to the data collection device 200, and in response to determining that the data extraction device 300 is not connected to the data collection device 200, determine to establish a data storage path which allows biosignal data collected by the data collection device 200 to be stored in a memory of the data collection device 200 via a microcontroller (MCU) of the data collection device 200, and in response to determining that the data extraction device 300 is connected to the data collection device 200, determine to establish a data extraction path which allows an interface of the data extraction device 300 to directly connect to the memory of the data collection device 200 not via the MCU of the data collection device 200, thereby enabling high-speed transmission of large-sized biosignal data stored in the memory of the data collection device 200 to the external data extraction device 300, while maintaining low-power performance of the data collection device 200 as a wearable device.

Here, the biosignal data may include a variety of biosignal data such as an electrocardiogram, heart rate, brain wave, and pulse. However, the biosignal data according to the invention is not necessarily limited only to those listed above, and may be diversely expanded as long as the objects of the invention may be achieved.

Meanwhile, the data collection device 200 according to one embodiment of the invention may include a program module such as an application or a widget for supporting storage and extraction of biosignal data according to the invention. Further, the program module may be downloaded from an external application distribution server (not shown), an external system (not shown), or the like.

The configuration and functions of the data collection device 200 according to the invention will be discussed in detail below. Meanwhile, the above description is illustrative although the data collection device 200 has been described as above, and it is noted that at least a part of the functions or components required for the data collection device 200 may be implemented or included in the data extraction device 300 to be described below or an external system (not shown), as necessary.

Next, the data extraction device 300 according to one embodiment of the invention is equipment capable of connecting to and communicating with the above-described data collection device 200, or communicating with another device (not shown) or a server (not shown) via the communication network 100, and may function to extract the biosignal data stored in the memory of the data collection device 200 at high speed via the data extraction path provided by the data collection device 200.

Specifically, the data extraction device 300 according to one embodiment of the invention may implement a high-speed clock using an external power source provided separately from the data collection device 200. Further, the data extraction device 300 according to one embodiment of the invention may include a high-speed quad serial peripheral interface (SPI), a high-speed USB controller, and the like required for high-speed extraction of large-sized biosignal data.

In addition, the data extraction device 300 according to one embodiment of the invention may further include a high-performance application processor (AP), an Ethernet controller, a WiFi controller, and the like required for wireless transmission of large-sized biosignal data extracted at high speed.

Meanwhile, the above description is illustrative although the data extraction device 300 has been described as above, and it is noted that at least a part of the functions or components required for the data extraction device 300 may be implemented or included in the data collection device 200, as necessary.

Configuration of the Data Collection Device

Hereinafter, the internal configuration of the data collection device 200 crucial for implementing the invention and the functions of the respective components thereof will be discussed.

Figure 3:
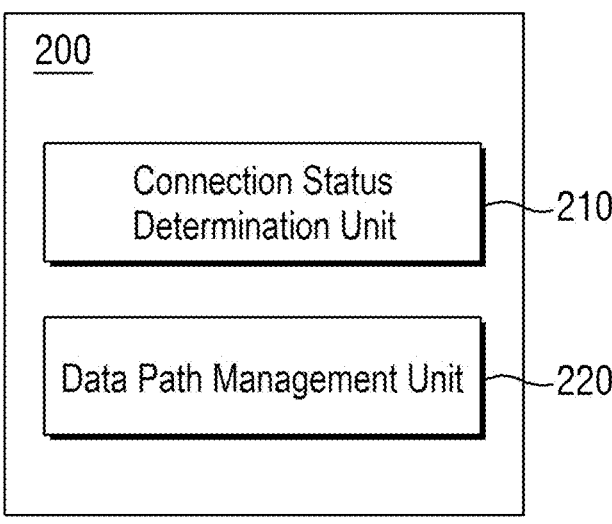

FIG. 3 illustratively shows the configuration of the data collection device according to one embodiment of the invention.

The data collection device 200 according to one embodiment of the invention may comprise a connection status determination unit 210 and a data path management unit 220. According to one embodiment of the invention, at least some of the connection status determination unit 210 and the data path management unit 220 may be program modules that communicate with an external system. The program modules may be included in the data collection device 200 in the form of operating systems, application program modules, and other program modules, while they may be physically stored in a variety of commonly known storage devices. Further, the program modules may also be stored in a remote storage device that may communicate with the data collection device 200. Meanwhile, such program modules may include, but are not limited to, routines, subroutines, programs, objects, components, and data structures for performing specific tasks or executing specific abstract data types according to the invention as will be described below.

First, the connection status determination unit 210 according to one embodiment of the invention may function to determine whether the data extraction device 300 is connected to the data collection device 200.

Specifically, since the data extraction device 300 is provided with an external power source required for high-speed extraction of large-sized data, the connection status determination unit 210 according to one embodiment of the invention may determine whether the data extraction device 300 is physically connected to a data communication line of the data collection device 200 by detecting the external power source of the data extraction device 300 using an external power source detection means. Further, the connection status determination unit 210 according to one embodiment of the invention may determine whether the data extraction device 300 is connected to the data communication line of the data collection device 200 on the basis of detection information acquired through separate communication between a microcontroller of the data collection device 200 and the data extraction device 300.

Next, in response to determining that the data extraction device 300 is not connected to the data collection device 200, the data path management unit 220 according to one embodiment of the invention may determine to establish a data storage path which allows biosignal data collected by the data collection device 200 to be stored in a memory of the data collection device 200 via a microcontroller (MCU) of the data collection device 200.

Specifically, according to one embodiment of the invention, when the data storage path is established, the biosignal data may be transmitted at a speed of several hundred kbps to several Mbps and stored in the memory through a serial interface (e.g., I2C or SPI) that the microcontroller and memory of the data collection device 200 have in common, and the microcontroller of the data collection device 200 may execute a predetermined data compression process to minimize the size of the biosignal data stored in the memory.

That is, according to one embodiment of the invention, in a normal state in which the data extraction device 300 is not connected to the data collection device 200, data on a biosignal sensed and measured by a sensor module may be stored in the memory through a data interface provided by the microcontroller of the data collection device 200, thereby maintaining low-power performance of the data collection device 200 as a wearable device.

Further, in response to determining that the data extraction device 300 is connected to the data collection device 200, the data path management unit 220 according to one embodiment of the invention may determine to establish a data extraction path which allows an interface of the data extraction device 300 to directly connect to the memory of the data collection device 200 not via the MCU of the data collection device 200.

Specifically, according to one embodiment of the invention, when the data extraction path is established, the biosignal data stored in the memory of the data collection device 200 may be extracted directly through a data interface of the data extraction device 300, not via the microcontroller of the data collection device 200, and power required to operate the memory of the data collection device 200 at high speed to extract large-sized biosignal data at high speed may be supplied from the power source of the data extraction device 300.

That is, according to one embodiment of the invention, in a data extraction state in which the data extraction device 300 is connected to the data collection device 200, large-sized biosignal data stored in the memory of the data collection device 200 may be extracted at high speed using the data interface and power source of the data extraction device 300, without consuming resources of the microcontroller of the data collection device 200.

Specifically, in response to determining that the data extraction device is not connected to the data collection device, the data path management unit 220 according to one embodiment of the invention may connect a path corresponding to the data storage path and disconnect a path corresponding to the data extraction path, among data transmission paths in the data collection device.

In contrast, in response to determining that the data extraction device is connected to the data collection device, the data path management unit 220 according to one embodiment of the invention may disconnect a path corresponding to the data storage path and connect a path corresponding to the data extraction path, among the data transmission paths in the data collection device.

Figure 4:
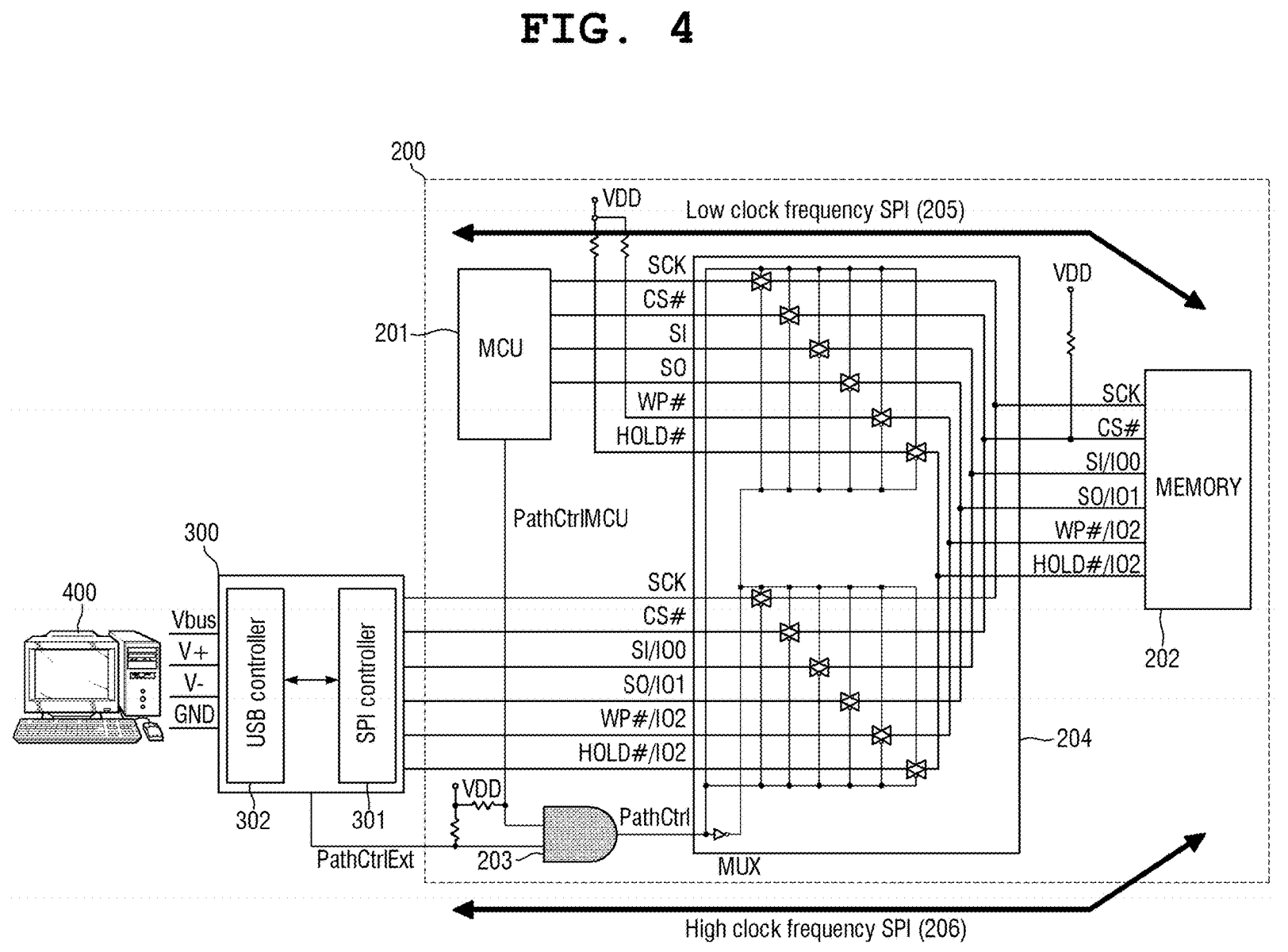
Figure 5:
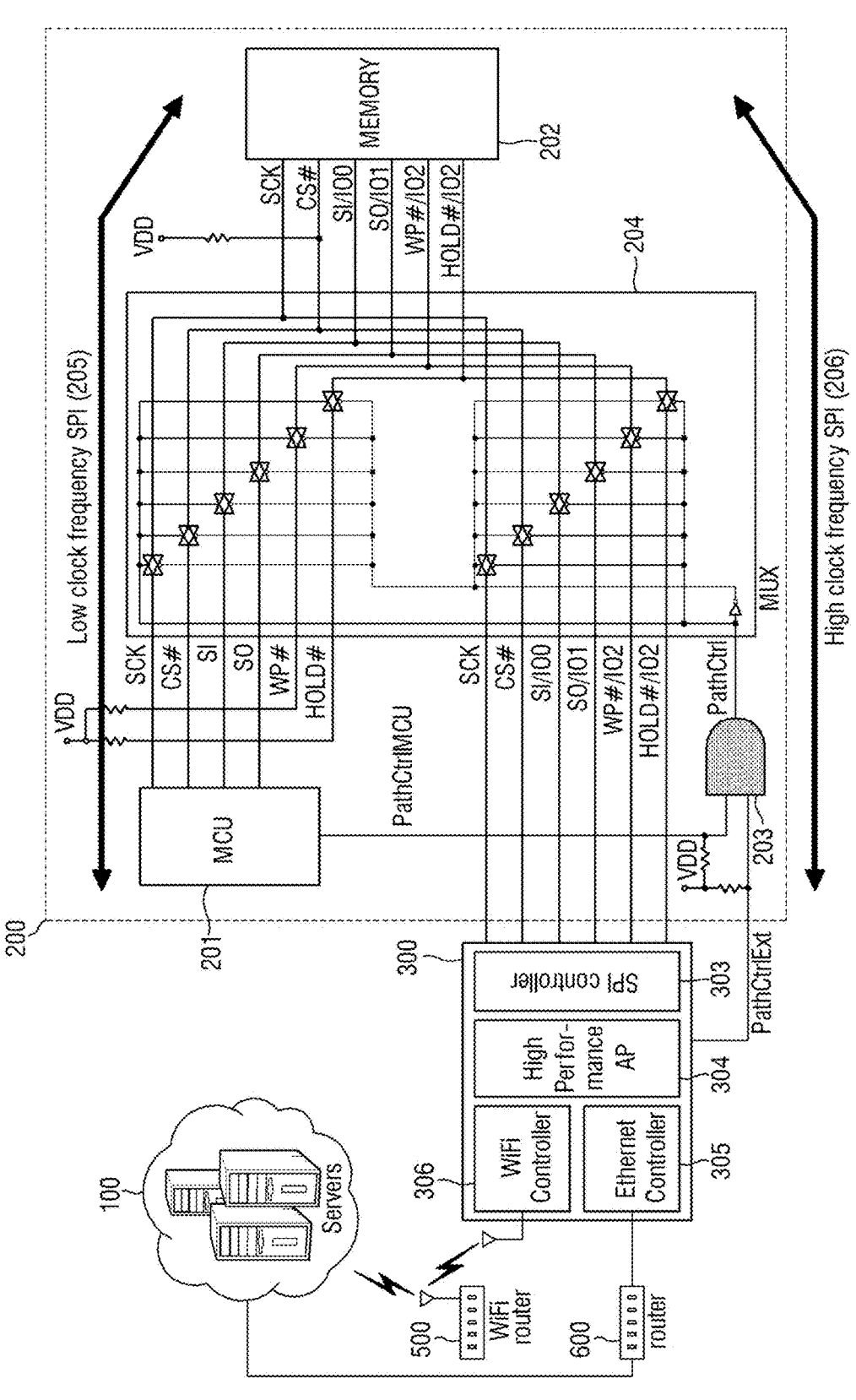
FIG. 5 illustratively shows how biosignal data stored in a data collection device is extracted to a data extraction device according to one embodiment of the invention.

FIGS. 4 and 5 illustratively show how biosignal data stored in the data collection device is extracted to the data extraction device according to one embodiment of the invention.

First, referring to FIG. 4, in a normal state in which biosignal data sensed or measured from a user's body is stored in a memory 202 in the data collection device 200, a data path corresponding to a high clock frequency SPI for connecting the memory 202 and the data extraction device 300 within a MUX 204 may be disconnected and a data path corresponding to a low clock frequency SPI for connecting the memory 202 and a MCU 201 may be connected, as a gate 203 is controlled by a PathCtrlMCU signal and a PathCtrl signal.

Further, referring to FIG. 4, when the data extraction device 300 is connected to the data collection device 200 and the biosignal data stored in the memory 202 is extracted, the data path corresponding to the high clock frequency SPI for connecting the memory 202 and the data extraction device 300 within the MUX 204 may be connected and the data path corresponding to the low clock frequency SPI for connecting the memory 202 and the MCU 201 may be disconnected, as the gate 203 is controlled by a PathCtrlExit signal and a PathCtrl signal.

Referring further to FIG. 4, the data extraction device 300 may include a high-speed SPI controller 301 and a high-speed USB controller 302, so that large-sized biosignal data may be extracted at high speed and then transmitted to an external device or a server without loss or delay.

Next, referring to FIG. 5, the data extraction device 300 may include a high-speed SPI controller 303, a high-performance application processor (AP) 304, an Ethernet controller 305, and a WiFi controller 306, so that large-sized biosignal data may be extracted at high speed and then uploaded to a cloud server at high speed via a wireless communication network.

According to one embodiment of the invention, the data extraction path may support data transmission at a dramatically higher speed compared to the data storage path.

For example, it may be assumed that biosignal data with a resolution of 12 bits is measured for 7 days at a sampling rate of 500 samples/sec and stored in the memory of the data collection device 200, so that the size of the biosignal data stored in the memory of the data collection device 200 is about 3.6 Gbit. In this case, when the biosignal data stored in the memory of the data collection device 200 is extracted at high speed with a clock frequency of 30 MHz using a 4-bit SPI, it is possible to extract all the biosignal data with the large size of about 3.6 Gbit in a short time of about 30.2 seconds.

The embodiments according to the invention as described above may be implemented in the form of program instructions that can be executed by various computer components, and may be stored on a computer-readable recording medium. The computer-readable recording medium may include program instructions, data files, and data structures, separately or in combination. The program instructions stored on the computer-readable recording medium may be specially designed and configured for the present invention, or may also be known and available to those skilled in the computer software field. Examples of the computer-readable recording medium include the following: magnetic media such as hard disks, floppy disks and magnetic tapes; optical media such as compact disk-read only memory (CD-ROM) and digital versatile disks (DVDs); magneto-optical media such as floptical disks; and hardware devices such as read-only memory (ROM), random access memory (RAM) and flash memory, which are specially configured to store and execute program instructions. Examples of the program instructions include not only machine language codes created by a compiler, but also high-level language codes that can be executed by a computer using an interpreter. The above hardware devices may be changed to one or more software modules to perform the processes of the present invention, and vice versa.

Although the present invention has been described above in terms of specific items such as detailed elements as well as the limited embodiments and the drawings, they are only provided to help more general understanding of the invention, and the present invention is not limited to the above embodiments. It will be appreciated by those skilled in the art to which the present invention pertains that various modifications and changes may be made from the above description.

Therefore, the spirit of the present invention shall not be limited to the above-described embodiments, and the entire scope of the appended claims and their equivalents will fall within the scope and spirit of the invention.

What is claimed is:

1. A method for extracting biosignal data, the method comprising steps of:

determining whether a data extraction device is connected to a data collection device; and in response to determining that the data extraction device is not connected to the data collection device, determining to establish a data storage path which allows the biosignal data collected by the data collection device to be stored in a memory of the data collection device via a microcontroller (MCU) of the data collection device, and in response to determining that the data extraction device is connected to the data collection device, determining to establish a data extraction path which allows an interface of the data extraction device to directly connect to the memory of the data collection device not via the MCU of the data collection device, wherein in response to said determining that the data extraction device is not connected to the data collection device, a first path corresponding to the data storage path is connected and a second path corresponding to the data extraction path is disconnected, among data transmission paths in the data collection device, and in response to determining that the data extraction device is connected to the data collection device, a third path corresponding to the data storage path is disconnected and a fourth path corresponding to the data extraction path is connected, among the data transmission paths in the data collection device.

2. The method of claim 1, wherein the data collection device is a wearable device for constantly collecting the biosignal data from a user's body.

3. The method of claim 1, wherein the data extraction path supports data transmission at a relatively higher speed compared to the data storage path, on a basis of resources of the data extraction device.

4. A non-transitory computer-readable recording medium having stored thereon a computer program for executing a method for extracting biosignal data, the method comprising steps of:

determining whether a data extraction device is connected to a data collection device; and in response to determining that the data extraction device is not connected to the data collection device, determining to establish a data storage path which allows the biosignal data collected by the data collection device to be stored in a memory of the data collection device via a microcontroller (MCU) of the data collection device, and in response to determining that the data extraction device is connected to the data collection device, determining to establish a data extraction path which allows an interface of the data extraction device to directly connect to the memory of the data collection device not via the MCU of the data collection device, wherein in response to said determining that the data extraction device is not connected to the data collection device, a first path corresponding to the data storage path is connected and a second path corresponding to the data extraction path is disconnected, among data transmission paths in the data collection device, and in response to determining that the data extraction device is connected to the data collection device, a third path corresponding to the data storage path is disconnected and a fourth path corresponding to the data extraction path is connected, among the data transmission paths in the data collection device.

5. A device for extracting biosignal data, the device comprising:

a connection status determination unit configured to determine whether a data extraction device is connected to a data collection device; and a data path management unit configured to, in response to determining that the data extraction device is not connected to the data collection device, determine to establish a data storage path which allows the biosignal data collected by the data collection device to be stored in a memory of the data collection device via a microcontroller (MCU) of the data collection device, and in response to determining that the data extraction device is connected to the data collection device, determine to establish a data extraction path which allows an interface of the data extraction device to directly connect to the memory of the data collection device not via the MCU of the data collection device, wherein in response to said determining that the data extraction device is not connected to the data collection device, a first path corresponding to the data storage path is connected and a second path corresponding to the data extraction path is disconnected, among data transmission paths in the data collection device, and in response to determining that the data extraction device is connected to the data collection device, a third path corresponding to the data storage path is disconnected and a fourth path corresponding to the data extraction path is connected, among the data transmission paths in the data collection device.

6. The system of claim 5, wherein the data collection device is a wearable device for constantly collecting the biosignal data from a user's body.

7. The system of claim 5, wherein the data extraction path supports data transmission at a relatively higher speed compared to the data storage path, on the basis of resources of the data extraction device.

\* \* \* \* \*